(12) United States Patent  
McIntire et al.

(10) Patent No.: US 7,826,882 B2
(45) Date of Patent: Nov. 2, 2010

(54) ELECTRODE LEAD SET FOR MEASURING PHYSIOLOGIC INFORMATION

(75) Inventors: James Francis McIntire, West Linn, OR (US); Brian Erik Haug, Portland, OR (US); Doris Arlene Beck, Beaverton, OR (US); Arthur Glen Buck, Sherwood, OR (US)

(73) Assignee: Tyco Electronics Corporation, Berwyn, PA (US)

( * ) Notice: Subject to any disclaimer, the term of this patent is extended or adjusted under 35 U.S.C. 154(b) by 323 days.

(21) Appl. No.: 11/732,373

(22) Filed: Apr. 3, 2007

(65) Prior Publication Data

US 2008/0249390 A1 Oct. 9, 2008

(51) Int. Cl.
*A61B 5/0408* (2006.01)
(52) U.S. Cl. .................. 600/393; 600/394; 439/909
(58) Field of Classification Search ........... 600/393, 600/394; 439/909
See application file for complete search history.

(56) References Cited

U.S. PATENT DOCUMENTS

| | | | | |
|---|---|---|---|---|
| 3,895,635 | A | * | 7/1975 | Justus et al. .................. 606/32 |
| 4,102,331 | A | * | 7/1978 | Grayzel et al. ............... 600/385 |
| 4,304,453 | A | * | 12/1981 | Grunwald .................... 439/341 |
| 4,353,372 | A | | 10/1982 | Ayer |
| 4,539,995 | A | * | 9/1985 | Segawa ....................... 600/385 |
| 4,674,511 | A | | 6/1987 | Cartmell |
| 4,702,256 | A | | 10/1987 | Robinson et al. |
| 5,062,426 | A | * | 11/1991 | Ulbrich et al. ............... 600/391 |
| 5,327,888 | A | | 7/1994 | Imran |
| 5,341,806 | A | * | 8/1994 | Gadsby et al. ............... 600/393 |
| 5,546,950 | A | | 8/1996 | Schoeckert et al. |
| 5,868,671 | A | | 2/1999 | Mahoney |
| 6,032,064 | A | | 2/2000 | Devlin et al. |
| 6,611,705 | B2 | | 8/2003 | Hopman et al. |
| 6,847,836 | B1 | | 1/2005 | Sujdak |
| 7,445,522 | B2 | * | 11/2008 | Burnes et al. ............... 439/725 |
| 2003/0130585 | A1 | | 7/2003 | Wenger |
| 2005/0251004 | A1 | | 11/2005 | Istvan et al. |

FOREIGN PATENT DOCUMENTS

| | | | |
|---|---|---|---|
| GB | | 2047947 A | 12/1980 |
| WO | WO 94/03907 A | | 2/1994 |

OTHER PUBLICATIONS

International Search Report for International Application No. PCT/US2008/004421, mailed Jul. 18, 2008.
International Search Report for International Application No. PCT/US2008/004425, mailed Jul. 18, 2008.

* cited by examiner

*Primary Examiner*—Lee S Cohen

(57) ABSTRACT

An electrode lead set is provided for electrical connection to a body. The electrode lead set includes a flexible ribbonized cable core extending between a proximal end portion and a distal end portion. The distal end portion includes a plurality of branch end portions that are each configured to hold an electrode. The flexible ribbonized cable core is separable into a plurality of branches that are each joined to adjacent branches by a separable interface prior to separation. Each of the plurality of branches includes a corresponding one of the branch end portions. Each of the plurality of branches includes a generally planar ribbon conductor extending along the corresponding branch from the proximal end portion of the ribbonized cable core to the corresponding branch end portion.

16 Claims, 8 Drawing Sheets

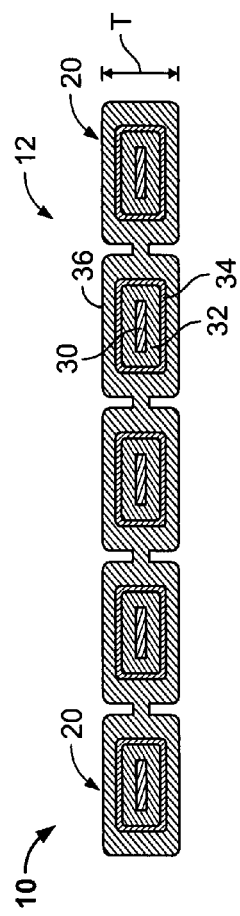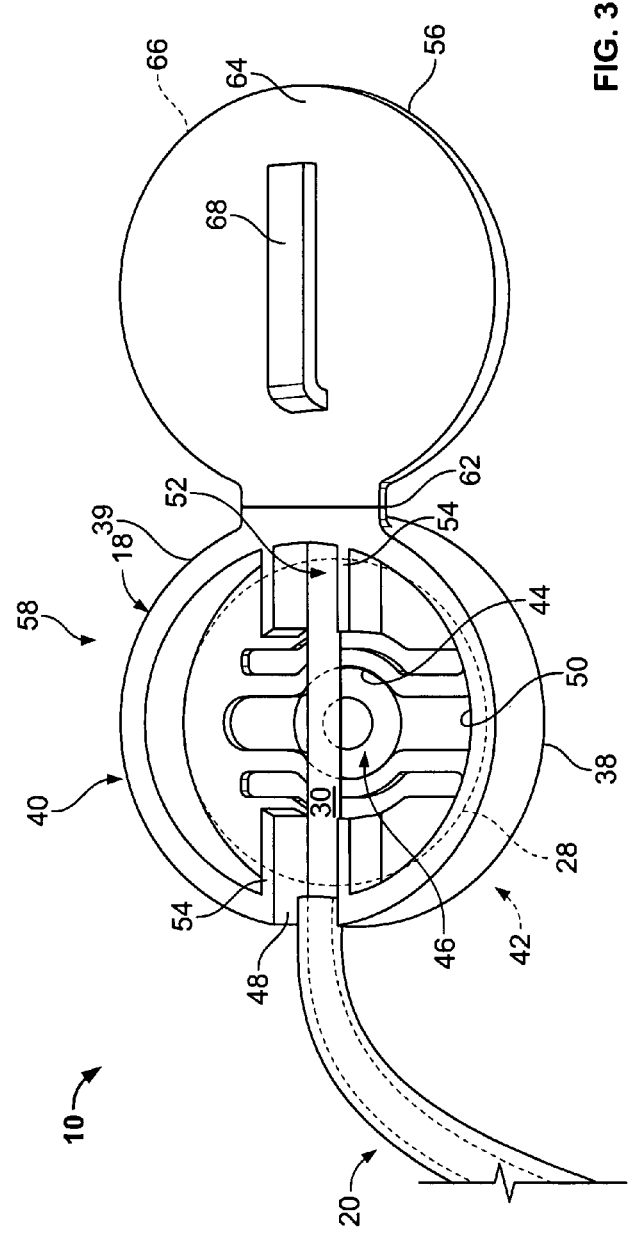

ELECTRODE LEAD SET FOR MEASURING PHYSIOLOGIC INFORMATION

BACKGROUND OF THE INVENTION

The invention relates generally to electrode lead sets, and, more particularly, to electrode lead sets for measuring physiologic information.

An electrocardiograph (ECG) system monitors heart electrical activity in a patient. Conventional ECG systems utilize electrodes placed on a patient in specific locations to detect electrical impulses generated by the heart during each beat. Typically, the electrical impulses or signals are detected by and directly transferred from the electrodes to a stationary ECG monitor via multiple cables or wires. The ECG monitor performs various signal processing and computational operations to convert the raw electrical signals into meaningful information that can be displayed on a monitor or printed out for review by a physician.

ECG measurements are taken by applying electrodes to different chest locations and additional body locations, such as the arms and legs. In the past, each of the electrodes has been connected to the ECG monitor by a separate shielded lead. However, the separate leads sometimes become entangled with each other during use and/or during application of the electrodes to the various body locations. Entanglement of the leads may make it more difficult and/or time-consuming to apply the electrodes, which may delay diagnosis and/or increase the time, and therefore cost, of the ECG procedure, as well as possibly inconveniencing the patient. Entanglement of the leads may be a minor inconvenience during routine medical procedures, such as an annual check-up. However, entanglement may be life threatening during emergency situations in which an immediate ECG read-out is critical.

To reduce entanglement of the electrode leads, some known ECG systems embed the electrodes and the corresponding leads within an insulative sheet of material that is placed over the patient's chest area and/or the other additional body locations. The electrodes are embedded within the sheet at fixed locations that, when the insulative sheet is placed over the patient's body, correspond to the desired locations on the patient for taking ECG measurements. However, because body size and/or shape may vary greatly between different patients, the fixed location of one or more of the electrodes within the insulative sheet may not correspond to the desired location for taking ECG measurements on some patients. For example, the locations of electrodes within an insulative sheet designed for a man over six feet tall may not align with the desired locations for taking ECG measurements on the body of a woman who is about five feet tall. Accordingly, different insulative sheets may be designed for different body sizes and/or shapes, which may increase a cost of the insulative sheets as well as a cost of performing the ECG procedure.

Moreover, the leads of some known ECG systems are typically reused many times on a number of different patients over the field life of the ECG lead set. To prevent the transmission of infection between patients, the electrodes and leads are disinfected between uses. However, the disinfection process may add time and/or expense to the ECG procedure. Moreover, the disinfection process sometimes fails to completely disinfect the electrodes and/or leads, for example because of human or machine error. In some cases, the disinfection process may be neglected completely. As a result, patient-to-patient infection caused by the reuse of ECG electrode lead sets has become an area of concern among healthcare providers. In addition to the general concern for the patient's well being, settlements and/or law suits resulting from patient-to-patient infection can be costly for healthcare providers.

There is a need for an electrode lead set having leads that are less likely to be entangled, that accommodate differently sized and/or shaped patient bodies, and/or that facilitate reducing patient-to-patient infection.

BRIEF DESCRIPTION OF THE INVENTION

In one embodiment, an electrode lead set is provided for electrical connection to a body. The electrode lead set includes a flexible ribbonized cable core extending between a proximal end portion and a distal end portion. The distal end portion includes a plurality of branch end portions that are each configured to hold an electrode. The flexible ribbonized cable core is separable into a plurality of branches that are each joined to adjacent branches by a separable interface prior to separation. Each of the plurality of branches includes a corresponding one of the branch end portions. Each of the plurality of branches includes a generally planar ribbon conductor extending along the corresponding branch from the proximal end portion of the ribbonized cable core to the corresponding branch end portion.

In another embodiment, an electrode lead set assembly is provided for electrical connection to a body. The electrode lead set assembly includes a flexible ribbonized cable core extending between a proximal end portion and a distal end portion. The distal end portion includes a plurality of branch end portions. The flexible ribbonized cable core is separable into a plurality of branches that are each joined to adjacent branches by a separable interface prior to separation. Each of the plurality of branches includes a corresponding one of the branch end portions. Each of the plurality of branches includes a generally planar ribbon conductor extending along the corresponding branch from the proximal end portion of the ribbonized cable core to the corresponding branch end portion. A plurality of electrodes are each held by a corresponding branch end portion of a different branch of the plurality of branches.

In another embodiment, an electrode lead set is provided for electrical connection to a body. The electrode lead set includes a flexible ribbonized cable core extending between a proximal end portion and a distal end portion. The distal end portion includes a plurality of branch end portions that are each configured to hold an electrode. The flexible ribbonized cable core is separable into a plurality of branches that are each joined to adjacent branches by a separable interface prior to separation. Each of the plurality of branches includes a corresponding one of the branch end portions. Prior to separation, the plurality of branches are configured such that the branch end portions are maintained in an array at the distal end portion of the substrate core. Each branch end portion within the array is located at about the same distance from the proximal end portion of the ribbonized cable core.

BRIEF DESCRIPTION OF THE DRAWINGS

FIG. 2 is a cross-sectional view of the electrode lead set shown in FIG. 1 taken along line 2-2 of FIG. 1.

FIG. 3 is a perspective view of a portion of the electrode lead set shown in FIG. 1 illustrating an exemplary embodiment of an electrode housing of the electrode lead set.

FIG. 10 is a schematic diagram of an exemplary embodiment of an electrocardiogram (ECG) system that the electrode lead set embodiments described and illustrated herein may be used with.

FIG. 11 is a schematic diagram of an alternative exemplary embodiment of an electrocardiogram (ECG) system that the electrode lead set embodiments described and illustrated herein may be used with.

DETAILED DESCRIPTION OF THE INVENTION

Figure 1:
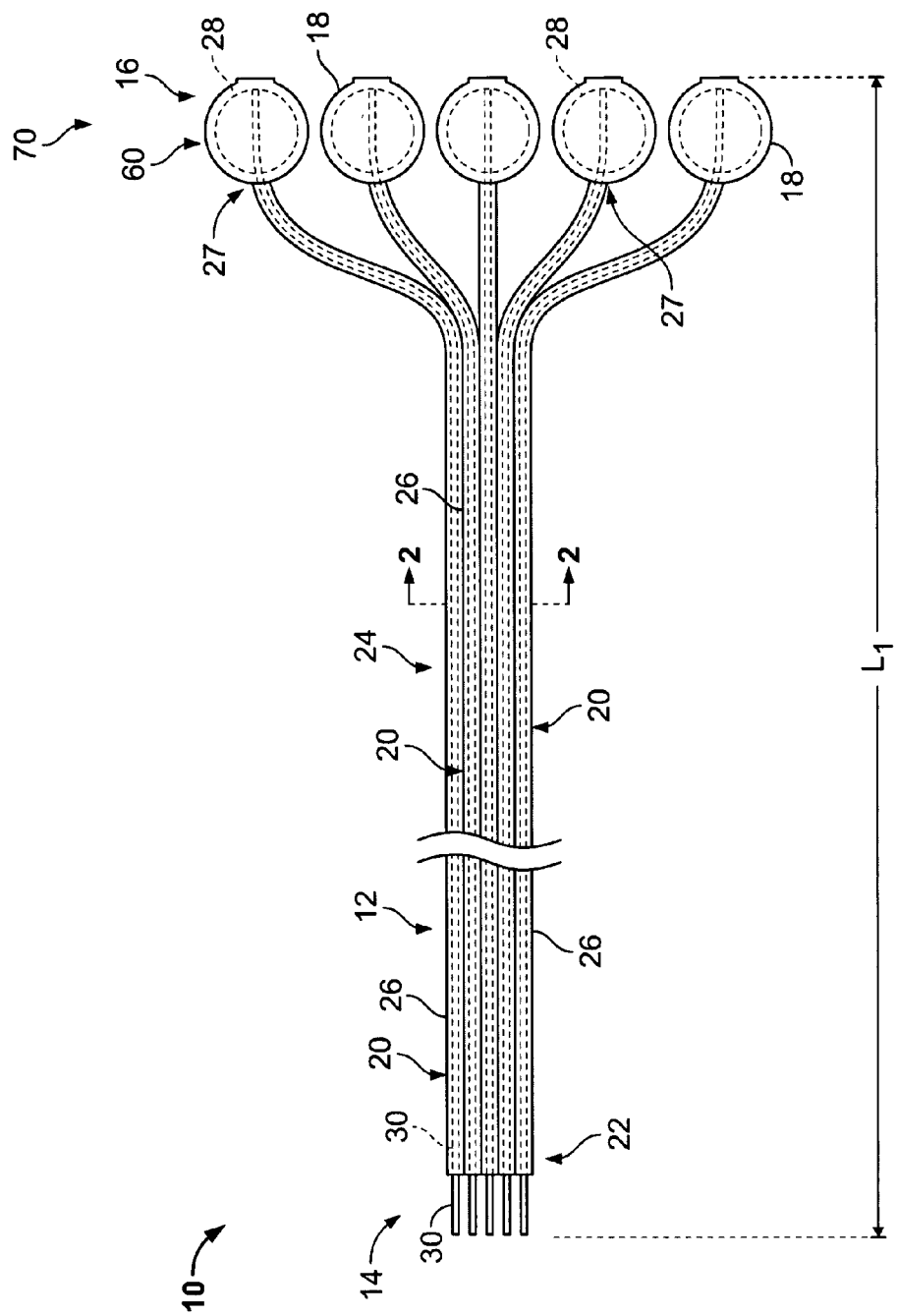
FIG. 1 is a top plan view of an exemplary embodiment of an electrode lead set for electrical connection to a body.

FIG. 1 is a plan view of an exemplary embodiment of an electrode lead set 10. The electrode lead set 10 includes a flexible ribbonized cable core 12 that extends along a length $L_1$ from a proximal end portion 14 to a distal end portion 16. The distal end portion 16 includes a plurality of electrode housings 18, as will be described in more detail below. The ribbonized cable core 12 is separable along a portion of the length of the ribbonized cable core 12 to define a plurality of branches 20. Specifically, the ribbonized cable core 12 includes a base portion 22 that includes the proximal end portion 14 and a branch portion 24 extending from the base portion 22 to the distal end portion 16. The ribbonized cable core 12 is separable along a separable interface 25 (FIG. 6) extending along at least a portion of the length of the branch portion 24 into the plurality of branches 20. Each branch 20 includes the corresponding electrode housing 18 and a stem 26 that extends from the base portion 22 to a corresponding branch end portion 27 that includes the electrode housing 18. Alternatively, one or more branches 20 do not include an electrode housing 18. Each branch 20 is configured to hold an electrode 28. For example, in the exemplary embodiment, and as will be described in more detail below, each of the electrode housings 18 holds an electrode 28. As will be described in more detail below, the electrodes 28 are configured to be placed at different locations on the body for measuring physiological information of the body.

The ribbonized cable core 12 may have any suitable size and/or shape that enables the electrode lead set 10 to function as described herein. In the exemplary embodiment, the ribbonized cable core 12 is generally planar, but the core 12 need not be planar.

FIG. 2 is a cross-sectional view of the ribbonized cable core 12 taken along line 2-2 of FIG. 1. Referring now to FIGS. 1 and 2, each branch 20 of the ribbonized cable core 12 includes an electrical conductor 30 that is generally planar and ribbon-shaped, and will be referred to herein as a ribbon conductor 30 or a generally planar ribbon conductor. Each ribbon conductor 30 extends along the length of the ribbonized cable core 12 between the proximal and distal end portions 14 and 16, respectively. Each ribbon conductor 30 extends along the length of a different stem 26 and along at least a portion of the length of the base portion 22. As will be described in more detail below, each of the ribbon conductors 30 is electrically connected to the corresponding electrode 28 to provide an electrical connection between the electrode 28 and a monitoring or other electronic device (e.g., the electrocardiogram (ECG) monitoring device 1002, shown in FIG. 10, and/or the hand-held patient monitor 1102, shown in FIG. 11) that may be connected to the base portion 22 at the proximal end portion 14, as will be described in more detail below.

In the exemplary embodiment, each of the ribbon conductors 30 is shielded along a portion of the length thereof. The ribbon conductors 30 may be shielded using any suitable arrangement, configuration, structure, means, and/or the like, for example, but not limited to, as shown in FIG. 2. Specifically, in the exemplary embodiment, each ribbon conductor 30 is at least partially surrounded by any suitable insulative material(s) 32, such as, but not limited to, polyvinyl chloride, polyethylene, and/or Electrodag® 1015 (commercially available from Acheson Colloids Company of Port Huron, Mich.). The insulative material 32 is at least partially surrounded by an electrically conductive material 34, which is at least partially surrounded by an electrically insulative jacket 36. Each of the insulative material 32, the electrically conductive material 34, and the jacket 36 extends along the length of the corresponding branch 20 from the corresponding electrode housing 18, along the corresponding stem 26, and along at least a portion of the base portion 22.

Each branch 20 may have any suitable thickness T that enables the electrode lead set 10 to function as described herein, such as, but not limited to, between about 0.040 inches (1.016 millimeters) and about 0.080 inches (2.032 millimeters). Moreover, a thickness of each of the ribbon conductors 30, the insulative material 32, the electrically conductive material 34, and the jacket 36 may be selected to provide a desired overall thickness T of each branch 20 and/or to provide a desired level of shielding. The ribbon conductors 30 may be fabricated from any suitable electrically conductive material(s) that enables the ribbon conductors 30 to electrically connect the electrodes 28 to the monitoring or other electronic device and/or that enables the electrode lead set 10 to function as described herein, such as, but not limited to, silver, aluminum, gold, copper, other metallic conductors, non-metallic conductors, and/or the like. The electrically conductive material 34 may be fabricated from any suitable electrically conductive material(s) that facilitates shielding the ribbon conductors 30 and/or enables the electrode lead set 10 to function as described herein, such as, but not limited to, silver, aluminum, gold, copper, other metallic conductors, non-metallic conductors, electrically conductive inks, other electrically conductive coatings, and/or the like. The jacket 36 may be fabricated from any suitable insulative material(s) that facilitates insulating and/or shielding the ribbon conductors 30 and/or that enables the electrode lead set 10 to function as described herein, such as, but not limited to, polyester (e.g., Mylar®), polyvinyl chloride, thermo-plastic-elastomer, and/or polyimide (e.g., Kapton®). The material(s) of the insulative material 32, the electrically conductive material 34, and/or the jacket 36 may be selected to provide a desired level of shielding.

FIG. 3 is a perspective view of a portion of the electrode lead set 10 illustrating an exemplary embodiment of the electrode housing 18. Each electrode housing 18 includes a body 38 having a side wall 39 extending between a pair of opposite end portions 40 and 42. The corresponding electrode 28 is held by the housing on the end portion 42. Although shown as generally circular, the body 38 of each of the electrode housings 18 may have any shape. The body 38 includes an opening 44 at the end portion 42 for receiving an electrical contact 46 of the corresponding electrode 28. The body 38 also includes an opening 48 within the side wall 39 that intersects an opening 50 within the body that extends through the end portion 40. A distal end portion 52 of the corresponding ribbon conductor 30 extends through the opening 48 into the opening 50. Optionally, the body 38 includes one or more guides 54 within the opening 50 for guiding placement of the ribbon conductor into the opening 50 and/or holding the distal end portion 52 of the ribbon conductor 30 in position within the opening 50. The openings 44, 48, and 50 are relatively arranged such that the electrical contact 46 of the corresponding electrode 28 engages, and is therefore electrically connected to, the distal end portion 52 of the ribbon conductor 30. The distal end portion 52 of the ribbon conductor 30 may be held within the opening 50 using any suitable structure, means, and/or the like, such as, but not limited to, an adhesive, stiction, and/or a snap-fit arrangement.

Optionally, the body 38 includes a cover 56 that is movable between an open position 58 shown in FIG. 3 and a closed position 60 (shown in FIG. 1). In the closed position 60, the cover 56 substantially covers the opening 50. In the exemplary embodiment, the cover 56 includes a hinge 62 that enables movement of the cover 56 between the open and closed positions 58 and 60, respectively. However, the cover 56 may include any other suitable structure, means, and/or the like that enables the cover 56 to be moved between the open and closed positions 58 and 60, respectively (whether the cover 56 remains attached to the body 38 in the open position 58 as in the exemplary embodiment). The cover 56 includes opposite side portions 64 and 66. The side portion 64 includes an extension 68 that is arranged such that when the cover 56 is in the closed position 60, the extension 68 engages and applies a force to a portion of the distal end portion 52 of the corresponding ribbon conductor 30 to facilitate holding the distal end portion 52 in engagement with, and therefore electrical connection to, the electrical contact 46 of the corresponding electrode 28. Optionally, the extension 68 moves the distal end portion 52 of the corresponding ribbon conductor 30 into engagement with the electrical contact 46 of the corresponding electrode in addition to facilitating the holding such engagement. In some embodiments, the extension 68 facilitates holding the distal end portion 52 of the corresponding ribbon conductor within the opening 50. The cover 56 may be secured in the closed position 60 using any suitable structure, means, and/or the like that enables the cover 56 to remain in the closed position 60 during use of the electrode lead set 10, such as, but not limited to, using a latch (not shown) and/or a snap-fit connection with a portion of the body 38 at the end portion 40.

Figure 4:
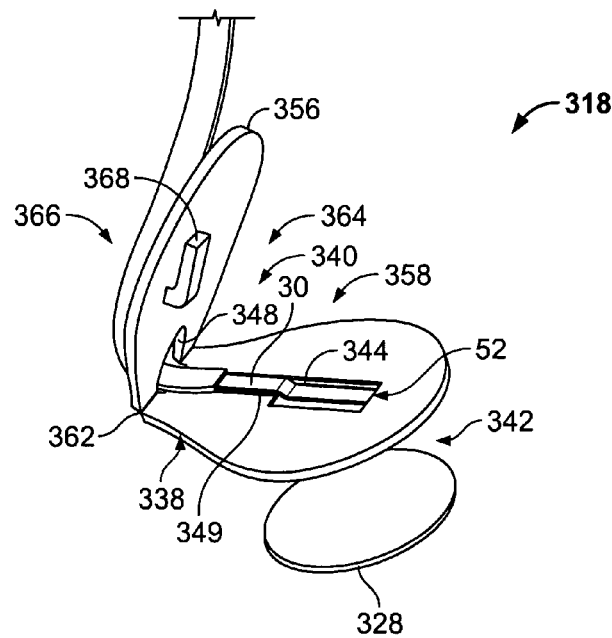
FIG. 4 is a partially exploded perspective view of an exemplary alternative embodiment of an electrode housing.

The shape, configuration, structure, and/or the like of the electrode housings 18, as well as any other alternative shapes, configuration, structures, and/or the like described and/or illustrated herein, are meant as exemplary only. The electrode housings are not limited to the shapes, configurations, structure, and/or the like described and/or illustrated herein. Rather, the electrode housings may have any suitable shape, configuration, structure, and/or the like that enables the electrode lead set embodiments described and/or illustrated herein to function as described herein. FIG. 4 illustrates an exemplary alternative embodiment of an electrode housing 318. The electrode housing 318 includes a body 338 having a pair of opposite end portions 340 and 342. A corresponding electrode 328 is held by the housing on the end portion 342. In the exemplary embodiment, the electrode 328 is an electrically conductive gel (described below) that is applied directly to the end portion 342 of the electrode housing body 338. However, any suitable type of electrode 328 may be used with, and held by, the electrode housing 318. Although shown as generally circular, the body 338 of the electrode housing 318 may have any shape. The body 338 includes an opening 344 at the end portion 342 and an opening 348 that receives a portion of the corresponding stem 26 therein. The distal end portion 52 of the corresponding ribbon conductor 30 extends through the opening 348, along a guide 349, and into the opening 344. In the exemplary embodiment, the electrode 328 directly engages, and is therefore directly electrically connected to, the distal end portion 52 of the ribbon conductor 30. Alternatively, the electrode 328 may be indirectly electrically connected to the distal end portion 52 of the ribbon conductor 30 via an electrical contact (not shown) of the electrode 328. The distal end portion 52 of the ribbon conductor 30 may be held within the opening 344 using any suitable structure, means, and/or the like, such as, but not limited to, an adhesive, stiction, and/or a snap-fit arrangement. In the exemplary embodiment, the distal end portion 52 is held within the opening at least partially by the cover 356 described below.

Optionally, the body 338 includes a cover 356 that is movable between an open position 358 shown in FIG. 4 and a closed position (not shown). In the closed position, the cover 356 substantially covers the opening 344. In the exemplary embodiment, the cover 356 includes a hinge 362 that enables movement of the cover 356 between the open and closed positions. However, the cover 356 may include any other suitable structure, means, and/or the like that enables the cover 356 to be moved between the open and closed positions (whether the cover 356 remains attached to the body 338 in the open position 358 as in the exemplary embodiment). The cover 356 includes opposite side portions 364 and 366. The side portion 364 includes an extension 368 that is arranged such that when the cover 356 is in the closed position, the extension 368 engages and applies a force to a portion of the distal end portion 52 of the corresponding ribbon conductor 30 to facilitate holding the distal end portion 52 in engagement with, and therefore electrical connection to, the electrode 328. Optionally, the extension 368 moves the distal end portion 52 of the corresponding ribbon conductor 30 into engagement with the electrode 328 in addition to facilitating the holding such engagement. In some embodiments, the extension 368 facilitates holding the distal end portion 52 of the corresponding ribbon conductor within the opening 344. The cover 356 may be secured in the closed position using any suitable structure, means, and/or the like that enables the cover 356 to remain in the closed position during use of the electrode lead set, such as, but not limited to, using a latch (not shown) and/or a snap-fit connection with a portion of the body 338 at the end portion 340.

Referring again to FIG. 1, the electrodes 28 may each be any suitable type of electrode that enables the electrodes 28 to function as described herein, such as, but not limited to, known ECG electrodes and/or suitable electrodes not currently known. For example, the electrodes 28 may be, but are not limited to being, of the type that includes an electrically conductive metal or other generally solid material and/or of the type that includes an electrically conductive fluid or gel. In the exemplary embodiment, the electrodes 28 are conventional snap fit electrodes 28, wherein the electrical contact 46 is a conventional snap-fit contact that extends outwardly from a body of the electrode 28 and connects to the body 38 of the electrode housing 18 using a snap-fit connection between the electrical contact 46 and a portion of the body 38 defining the opening 44. Other examples of suitable electrodes 28 include, but are not limited to, conventional tape electrodes, conventional tab electrodes, an electrically conductive pad and/or electrodes that include an electrically conductive fluid or gel contained within a membrane. Another example of the electrodes 28 includes an electrically conductive fluid or gel applied directly to the end portion 42 of the electrode housing 18 (e.g., the electrode 328 shown in FIG. 4 applied directly to the end portion 342 of the electrode housing 328). The electrically conductive pads, the conventional snap fit electrodes, the conventional tape electrodes, the conventional tab electrodes, the membranes having an electrically conductive fluid or gel, and the electrically conductive fluid or gel applied directly to the end portion 42 of the electrode housing 18 may directly connect to the distal end portion 52 of the corresponding ribbon conductor 30, for example through the opening 44, or may be electrically connected to the distal end portion 52 of the corresponding ribbon conductor 30 through an intermediate electrical contact (not shown). In addition or alternative to the snap-fit connection of the exemplary embodiment, the electrodes 28 may be connected to the end portion 42 of the electrode housings 18 using any suitable structure, means, and/or the like, such as, but not limited to, using stiction and/or an adhesive. In some embodiments, the adhesive may be or include an electrically conductive adhesive layer, such as, but not limited to, silver epoxy.

In some embodiments, prior to separation of the ribbonized cable core 12 into the plurality of branches 20, the electrode housings 18 are maintained in an array 70 having a pattern wherein each electrode housing 18 is located at about the same distance, or the length $L_1$, from the proximal end portion 14 of the ribbonized cable core 12. As used herein, the term "array" may include an ordered grouping of the electrode housings 18 and/or may include a collection of the electrode housings 18 that may be random, ordered, or a combination of random and ordered. The electrode housings 18 may be maintained in the array 70 using any suitable structure, means, and/or the like, such as, but not limited to, adhesive, a band (not shown) surrounding at least a portion of the electrode housings 18 and/or surrounding a portion of each of the stems 26 adjacent the housings 18, a base (not shown) connected to and common with each of the electrode housings 18, each of the electrodes 28, and/or the portion of each stem 26 adjacent the housings 18, and/or a separable interface (not shown) between adjacent housings 18, between the portion of each stem 26 adjacent the housings (such as, but not limited to, the separable interface 25 (FIG. 7) extended further along each stem 26 toward the housings 18), and/or between the housings 18 and adjacent stems 26. The base may include any suitable configuration, arrangement, structure, means, and/or the like that enables the base to hold the housings 18 in the array 70, such as, but not limited to, a sheet that is removably attached to each of the electrodes 28. The separable interface may include any suitable configuration, arrangement, structure, means, and/or the like that enables the separable interface to hold the housings 18 in the array 70, such as, but not limited to, perforated tape and/or perforations of any suitable size, shape, spacing, and/or frequency The pattern of the array 70, as well as any other alternative patterns described and/or illustrated herein, are meant as exemplary only. The electrode housings are not limited to uniform patterns, tiered patterns, symmetrical patterns, the specific patterns of the arrays 70, 170, and 270 shown in FIGS. 1, 5, and 6, respectively, or any other exemplary patterns described and/or illustrated herein. Rather, the electrode housings may have any suitable pattern that enables the electrode lead set embodiments described and/or illustrated herein to function as described herein.

Figure 5:
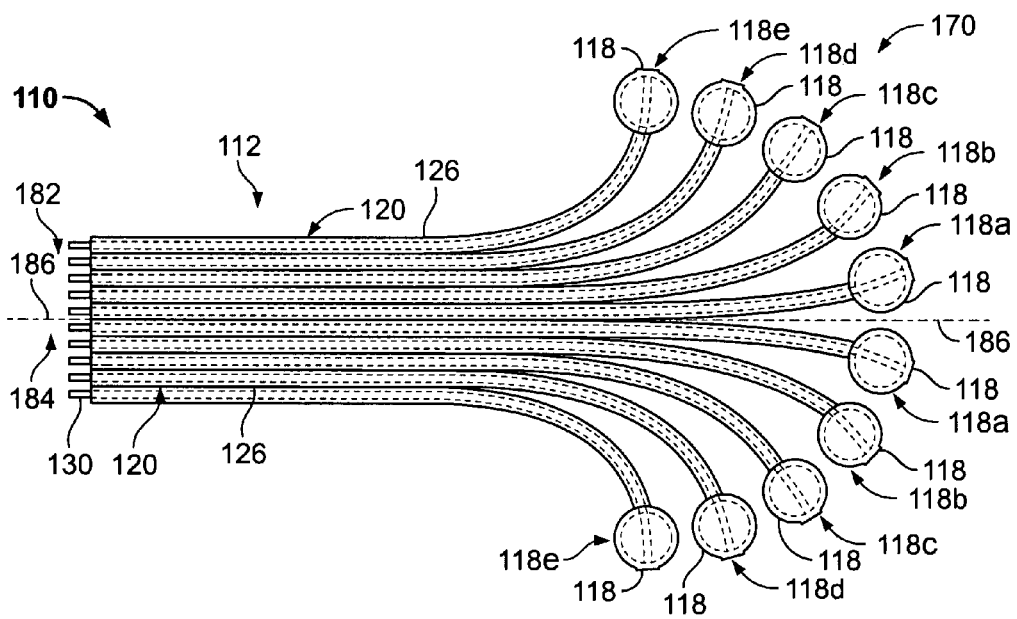
FIG. 5 is a top plan view of an exemplary alternative embodiment of an electrode lead set.

FIG. 5 illustrates an exemplary alternative embodiment of an electrode lead set 110. Each of the branches 120 includes a stem 126 having the same length, such that the electrode housings 118 may be held, prior to separation and for example as discussed above with respect to the array 70 (FIG. 1), in an array 170 wherein pairs 118*a, b, c, d,* and *e* of the electrode housings 118 are located on opposite sides 182 and 184 of a central longitudinal axis 186 of the ribbonized cable core 112 in a configuration that forms a "c" shape.

Figure 6:
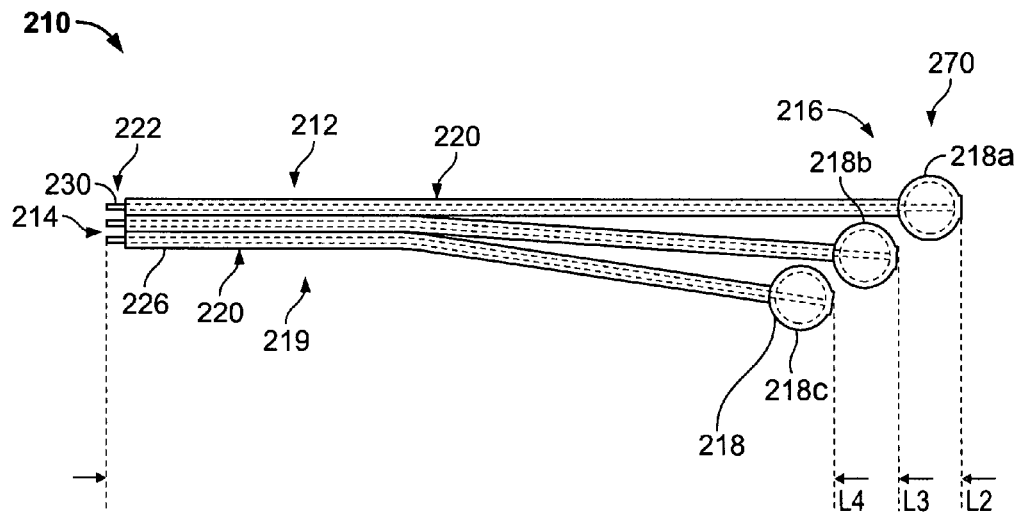
FIG. 6 is a top plan view of another exemplary alternative embodiment of an electrode lead set.

FIG. 6 illustrates another exemplary alternative embodiment of an electrode lead set 210. Prior to separation of a ribbonized cable core 212 into a plurality of branches 220, a plurality of electrode housings 218 may be held, for example as discussed above with respect to the array 70 (FIG. 1), in a tiered array 270 that includes an outermost (relative to a base portion 222) housing 218*a*, an innermost housing 218*c*, and an intermediate housing 218*b* held between the outermost and innermost housings 218*a* and 218*c*, respectively. The housings 218*a-c* are arranged in a tiered configuration where the outermost housing 218*a* is spaced a distance, or length $L_2$, measured from a proximal end portion 214 of the ribbonized cable core 212. Each successive housing 218*b* and 218*c* is located a shorter distance from the proximal end portion 214, denoted by a respective length $L_3$ and $L_4$ that is progressively shorter. A stem 226 connected to the housing 218*c* forms a portion of a side 219 of the ribbonized cable core 212. The stem 226 connected to each successive housing 218*b* and 218*a* (going in a direction toward a distal end portion 216 of the ribbonized cable core 212) within the tiered array 270 at least partially surrounds the stem 226 connected to any directly previous housing 218 within the tiered array 270.

Figure 7:
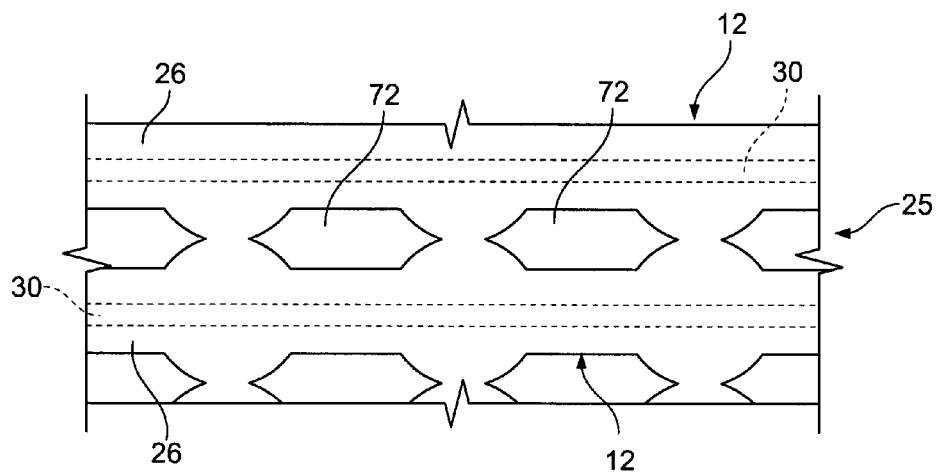
FIG. 7 is a top plan view of a portion of the electrode lead set shown in FIG. 1 illustrating an exemplary embodiment of a separable interface between branches of the electrode lead set.

Referring again to FIG. 1, as discussed above, the branches 20 of the ribbonized cable core 12 are joined along at least a portion of a length thereof to adjacent branches 20 by a separable interface 25 (FIG. 7). Although shown as being joined along the stems 26, in addition or alternative to the separable interface 25 along the stems 26, each branch 20 may be separably joined to each adjacent branch 20 at any portion thereof. Moreover, the separable interface 25 may include any suitable configuration, arrangement, structure, means, and/or the like that enables the ribbonized cable core 12 to be separable into the plurality of branches. For example, FIG. 7 illustrates the separable interface 25 of the exemplary embodiment wherein perforations 72 are provided along at least a portion of the length of each of the stems 26. Adjacent stems 26 can be separated by breaking the connections extending between each perforation 72. The perforations 72 may have any suitable size, shape, spacing, and/or frequency in addition or alternative to how the perforations 72 are illustrated in FIG. 7. The separable interface 25 of the exemplary embodiment is meant as exemplary only. Connection between adjacent branches 20 is not limited to the perforations 72, but rather the branches 20 may be connected using any suitable structure and/or means that enables separable connection between adjacent branches 20. For example, adjacent branches 20 may additionally or alternatively be connected together using a perforated tape. Moreover, the stems 26 may be connected at any number and location(s) along their length.

The exemplary arrangements shown in FIGS. 1, 5, and 6 allow the electrode housings, and therefore the electrodes, to be nested together as shown in the respective arrays 70, 170, and 270. The nested arrangement may facilitate reducing manufacturing costs by reducing an amount of material used to fabricate a plurality of the electrode lead sets. As discussed above, the arrangements shown in FIGS. 1, 5, and 6 are meant as exemplary only. The branches and the corresponding electrode housings and electrodes may have any other suitable relative arrangement that enables the electrode lead set to function as described herein. For example, the nested arrangement may be selected to facilitate placement of the electrodes at the desired locations on the body and/or to facilitate reducing manufacturing time, complexity, difficulty, and/or cost.

Figure 8:
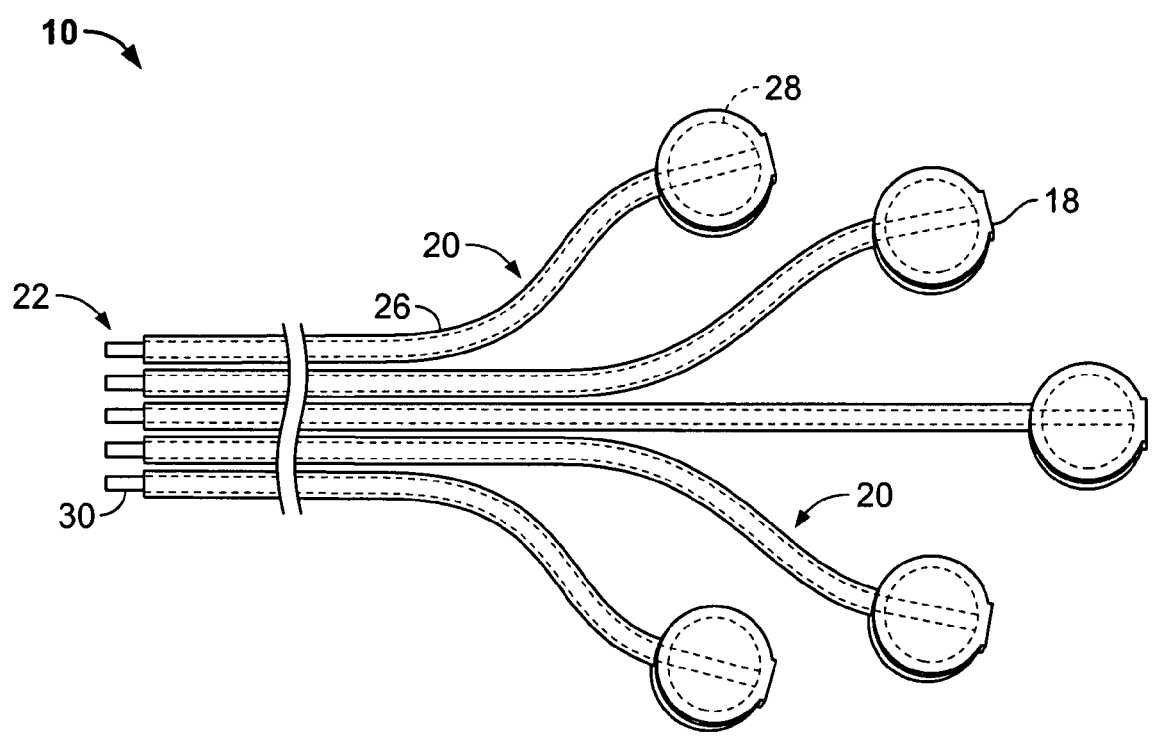
FIG. 8 is a perspective view of the electrode lead set shown in FIG. 1 illustrating the branches of the electrode lead set being separated.

In operation, and referring to FIGS. 1 and 8, the base portion 22 of the ribbonized cable core 12 is placed on or adjacent a patient's body (not shown in FIG. 1 or 8). Before the electrodes 28 are placed on the patient's body, the branches 20 are joined to each adjacent branch 20 by the separable interface 25 (FIG. 7). Each branch 20 can be separated from adjacent branches 20 by breaking the separable interface 25 between the branches 20. Once separated, a branch 20 can be manipulated to place the corresponding electrode 28 at the desired location on the patient's body. Because each branch 20 can be separately "peeled-away" from the other branches 20, the stems 26 of the branches 20 may be less likely to entangle during placement of the electrodes 28. Although the branches 20 may be less likely to entangle, some of the branches 20 may overlap when the electrodes 28 are placed at the desired locations. In some embodiments, the electrode housings 18 and/or the stems 26 include indicia (not shown) that indicates the desired location on the patient's body of the corresponding electrode 28.

FIG. 8 illustrates the electrode lead set 10 wherein the separable interface 25 (FIG. 7) between each pair of adjacent branches 20 has been broken. Once a branch 20 has been separated from the other branches 20, the branch 20 is only connected to the other branches 20 by the base portion 22. Because the ribbonized cable core 12 is generally flexible, and the branches 20 are only connected to each other by the base 22 (after separation), the stems 26 can bend along their length such that each electrode housing 18, and therefore each electrode 28, is selectively positionable at a plurality of different positions relative to the other electrodes 28. Specifically, the relative arrangement of the electrodes 28 is selectable such that each electrode 28 can be independently positioned without generally affecting the position of the other electrodes 28. Accordingly, the electrodes 28 may be positionable in a variety of relative arrangements to facilitate accommodating different patient body sizes and/or shapes. For example, electrodes 28 placed on the arm and leg of a patient may have a position relative to one another that is different than when the electrodes 28 are placed on the same portions of the arm and leg of another patient. The selective relative positioning of each of the electrodes 28 may allow for greater flexibility in using the electrode set 10 with different patients.

The branches 20 may have any suitable configuration, arrangement, pattern, and/or the like (whether when joined by the separable interfaces 25, shown in FIG. 7, or when separated) that enable the electrodes 28 to be placed at the desired locations on the body. For example, the electrode lead set 10 may include any number of branches 20 for positioning any number of electrodes 28 at any number of locations on the body. In the exemplary embodiment of FIGS. 1 and 8, the electrode lead set 10 includes five branches 20 for use within an ECG system (e.g., the ECG system 1000 shown in FIG. 10). For example, the electrodes 28 of four of the five branches 20 are configured to be placed at different limbs of a patient's body (e.g., both arms and both legs) and one of the five branches 20 is configured to be placed on the chest region of the body. An example of an alternative embodiment of the electrode lead set 10 includes only three branches 20 for use within an ECG system, wherein the electrodes 28 of the three branches 20 are configured to be placed at different limbs of the body (e.g., both arms and the left leg). Yet another example of an alternative embodiment of the electrode lead set 10 includes ten branches wherein the electrodes 28 of six of the branches 20 are configured to be placed at six different locations on a chest region of the body (e.g., the prescribed ECG precordial locations $V_1$, $V_2$, $V_3$, $V_4$, $V_5$, and $V_6$ of the American Heart Association (AHA) or the prescribed ECG precordial locations $C_1$, $C_2$, $C_3$, $C_4$, $C_5$, and $C_6$ of the International Electrotechnical Commission (IEC)) and the electrodes 28 of four branches 20 are configured to be placed on different limbs of the body (e.g., the prescribed locations RA, LA, RL, and LL of the AHA or the prescribed locations R, L, N, and F of the IEC). Even another example of an alternative embodiment of the electrode lead set 10 includes twelve branches 20 for use within an ECG system, wherein some of the electrodes 28 of the twelve branches 20 are configured to be placed at different limbs of the body and some of the electrodes 28 of the twelve branches 20 are configured to be placed on the chest region of the body. The electrode lead set embodiments described and/or illustrated herein are not limited to the three, five, ten, and twelve branch embodiments described and/or illustrated herein, but rather may include any number of branches for positioning any number of electrodes at any number of locations on the body.

The stems 26 of each of the branches 20 may have any suitable length that enables the corresponding electrode 28 to be placed at the corresponding desired location on the body. For example, in the exemplary embodiment of FIGS. 1 and 8 the stems 26 are each between about 15 inches (38.1 centimeters) and about 48 inches (121.9 centimeters) long. Another example is each stem 26 being between about 20 inches (50.8 centimeters) and about 32 inches (81.3 centimeters) long. The relative length of each of the stems 26, the pattern of any arrays of the electrode housings 18 and/or electrodes 28, and/or the particular location of each of the electrode housings 18 and/or electrodes 28 within the array and relative to each other (whether when joined by the separable interface 25 or when separated) may be selected to facilitate placement of each of the electrodes 28 at the desired locations.

The electrodes 28 may be sold or supplied to healthcare providers, or an intermediate party, as part of the electrode lead set 10, whether supplied or sold as attached to the electrode housings 18. Alternatively, the electrode lead set 10 may be supplied or sold to healthcare providers, or an intermediate party, without the electrodes 28 and the healthcare provider, or the intermediary party, may supply and attach electrodes 28 to the electrode housings 18, for example immediately prior to application of the electrodes 28 to the body. The electrodes 28 may be packaged together with the remainder of the electrode lead set 10 (whether attached to the pads 26) or alternatively the electrode lead set 10 may be packaged without including the electrodes 28 and the electrodes 28 may be provided in a separate package or provided by the healthcare provider or intermediate party.

The electrode lead set 10 may be packaged, whether including the electrodes 28, using any suitable packaging material(s), such as, but not limited to, paper and/or plastic. The paper, plastic, and/or other material(s) may be laminated and/or coated with any suitable material(s), such as, but not limited to, a metallic foil and/or a wax. The packaging material used to package the electrode lead set 10 may be sealed, for example, to facilitate preventing damage to, contamination of, and/or degradation of the any portion of the electrode lead set, for example during storage and/or shipping. The packaging material may be sealed using any suitable structure and/or means, such as, but not limited to, heat, adhesive, compression, and/or other fastening mechanisms that are capable of providing a seal. The packaging material may be hermetically sealed, for example, to facilitate preventing damage to, contamination of, and/or degradation of the any portion of the electrode lead set 10, for example, during storage and/or shipping. Moreover, in addition to the hermetic seal, the electrode lead set 10 may also be vacuum packaged. A portion(s) or an entirety of the electrode lead set 10 may be sterilized and/or disinfected prior to packaging.

In some embodiments, the electrode lead set 10 is disposable in that the electrode lead set is intended for a single use only. As used herein, the terms "disposable" and "single use" are intended to mean that a disposable, single use, electrode lead set 10 is used for one and only one patient, and thereafter discarded. For example, a disposable, single use, electrode lead set 10 may be used for one and only one procedure (e.g., an ECG measurement procedure) on one and only one patient, and thereafter discarded. Alternatively, a disposable electrode lead set 10 may be used for a plurality of procedures (e.g., a plurality of ECG measurement procedures, the plurality of procedures may be the same type of procedure or some or all of the plurality of procedures may be different procedure types) on one and only one patient, and thereafter discarded. When used for a plurality of procedures on one patient, the disposable, single use, electrode lead set 10, as a whole, is only applied to the patient one and only one time. However, some of the electrodes 28 of the disposable, single use, electrode lead set 10 may be repositioned on the one and only one patient within the range permitted by its stem 26 to accommodate different measurement locations for different procedure types and/or to obtain more accurate measurements. In other words, the electrode lead set 10 is not considered to be removed from the patient's body, as a whole, until all of the electrodes 28 are removed from the patient's body.

The electrodes 28 may be discarded along with the remainder of a disposable, single use, electrode lead set 10 after the single procedure or plurality of procedures. The material(s), size, shape, thickness(es), and/or any other properties, attributes, and/or the like of the electrode lead set 10 may be selected to facilitate providing and/or configured the electrical lead set 10 as disposable and single use. For example, material(s), size, shape, thickness(es), and/or any other properties, attributes, and/or the like of the ribbonized cable core 12, including but not limited to portions of the ribbonized cable core 12 such as the branches 20, may be selected to facilitate the providing and/or configuring the electrical lead set 10 as disposable and single use. The electrode lead set 10 may be configured and provided as disposable and single use, for example, to facilitate trying to reduce or prevent patient to patient infection and/or to facilitate trying to reduce or prevent operational costs, time, and/or workload resulting from sterilization and/or disinfection processes.

Figure 9:
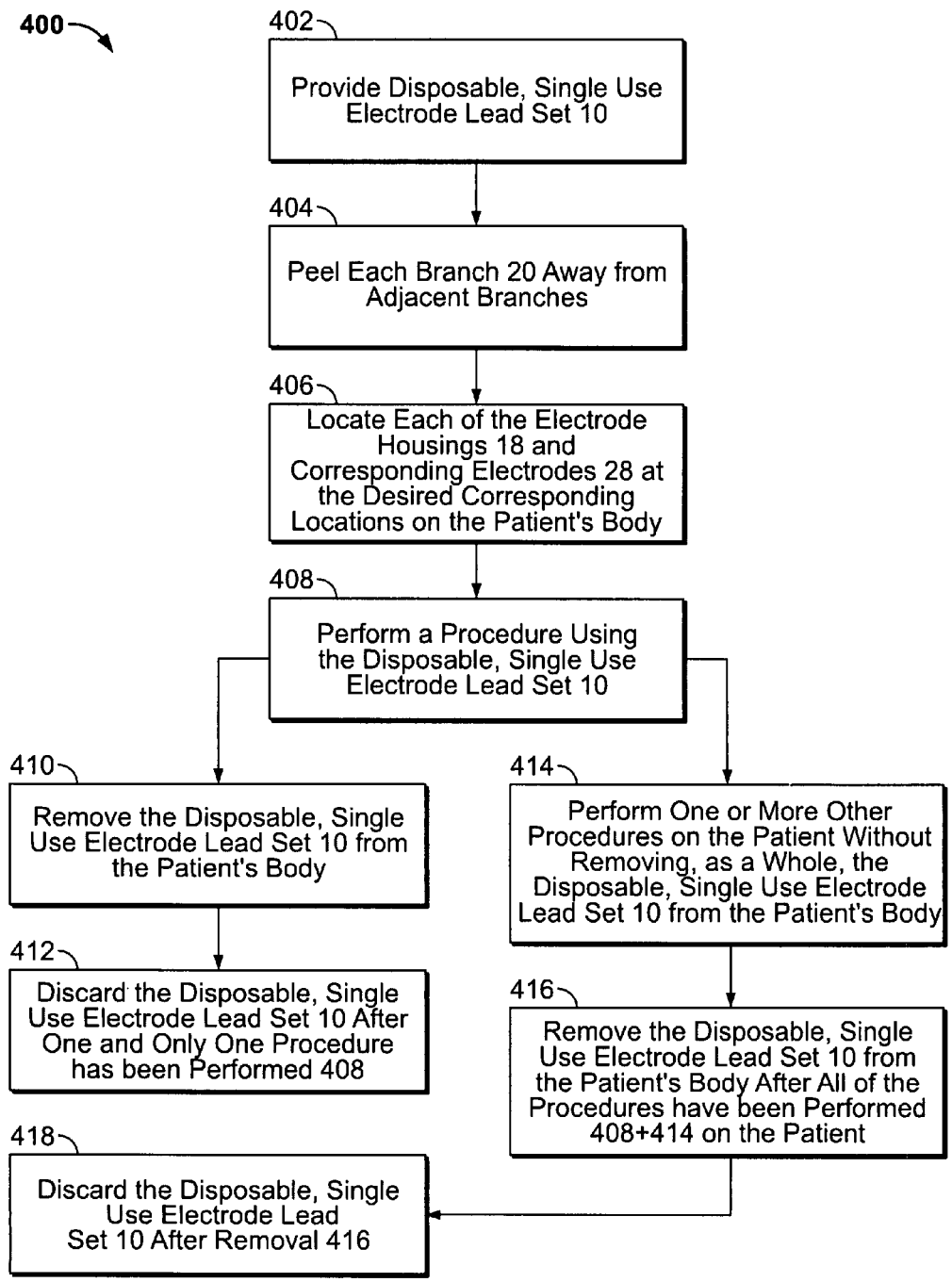
FIG. 9 illustrates one exemplary embodiment of a method of using the electrode lead set embodiments described and illustrated herein.

FIG. 9 illustrates one exemplary embodiment of a method 400 of using the electrode lead set embodiments described and illustrated herein. The method 400 includes providing 402 a disposable, single use, electrode lead set 10 for use with one and only one patient, peeling 404 each of the plurality of branches 20 away from adjacent branches 20, and locating 406 each of the electrode housings 18 and the corresponding electrodes 28, independently from one another, at the desired corresponding locations on the patient's body. Each branch 20 may be peeled 404 and located 406 prior to peeling 404 some or all of the other branches 20 (e.g., the branches 20 are peeled 404 and located 406 in succession, in any order; or two or more branches 20 may be peeled 404 and located 406 prior to peeling some of the other branches 20). Alternatively, all of the branches 20 are peeled 404 before any are located 406. The method 400 also includes performing 408 a procedure on the patient using the disposable, single use, electrode lead set 10. Optionally, the method 400 may include removing 410 the disposable, single use, electrode lead set 10 from the patient's body and discarding 412 the disposable, single use, electrode lead set 10 after one and only one procedure has been performed 408 on the patient using the set 10. Removal 410 includes removing all of the electrodes 28 from the patient's body. Moreover, the method 400 may alternatively include performing 414 one or more other procedures on the patient (whether some or all of the procedures are the same or different procedure types) without removing, as a whole, the disposable, single use, electrode lead set 10 from the patient's body, removing 416 the disposable, single use, electrode lead set 10 from the patient's body after all of the procedures have been performed 408 and 414 on the patient, and discarding 418 the disposable, single use, electrode lead set 10 after the removal 416. Removal 416 includes removing all of the electrodes 28 from the patient's body. In some embodiments, one or more electrodes 28 may be repositioned on the patient's body between procedures. The method 400 is meant as exemplary only. Embodiments of disposable electrode lead sets as described and illustrated herein are not limited to the exemplary method embodiment 400.

Figure 10:
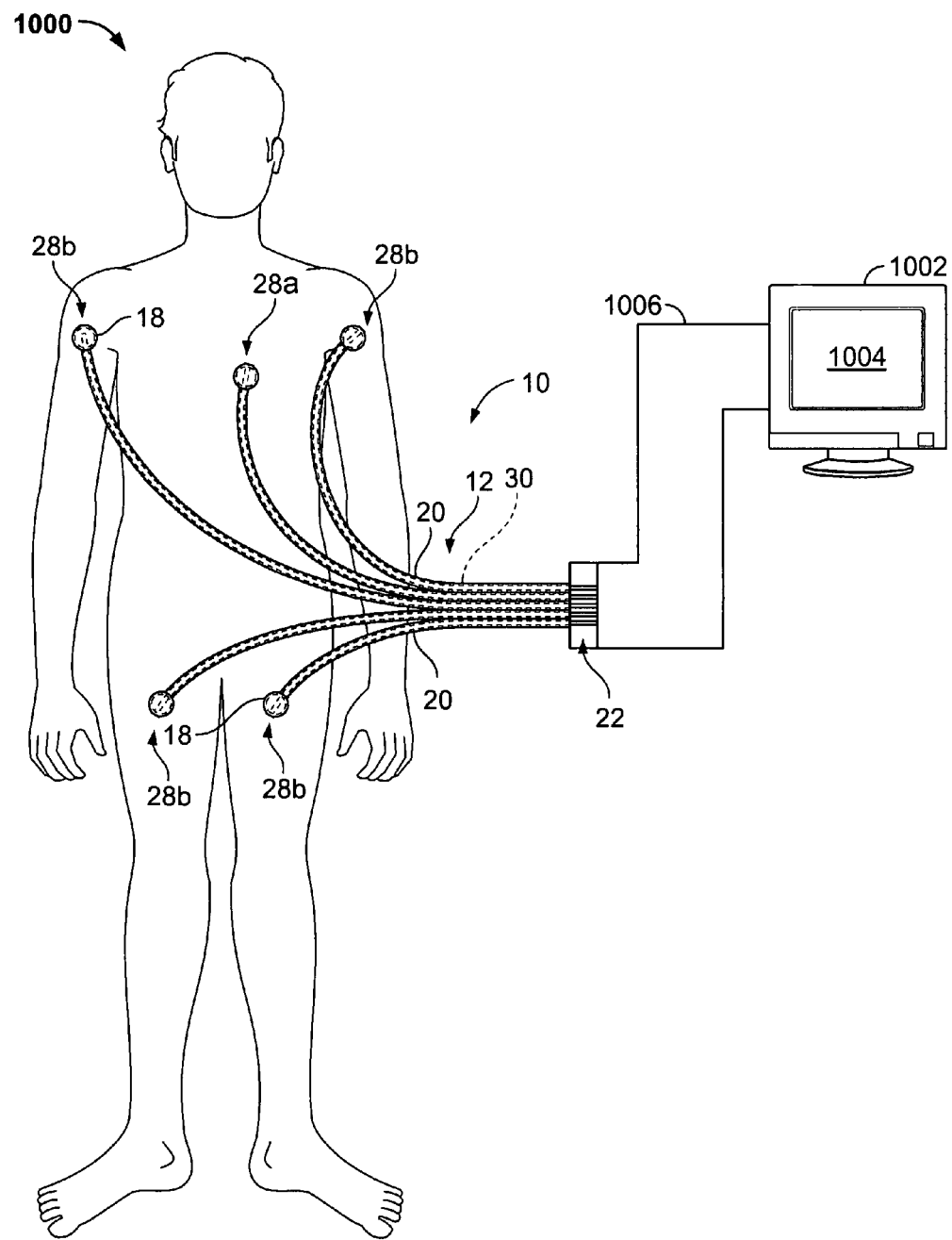

FIG. 10 is a schematic diagram of an exemplary embodiment of an ECG system 1000 that the electrode lead set embodiments described and illustrated herein may be, but are not limited to being, used with. The ECG system 1000 includes the electrode lead set 10 and an ECG monitoring device 1002. The base portion 22 of the electrode lead set 10 is connected to the ECG monitoring device 1002 such that the electrically conductive pathways 30 of each of the electrodes 28 are electrically connected to one or more corresponding circuits (not shown) of the ECG monitoring device 1002. The electrically conductive pathways 30 may be exposed through the jacket 36 (FIG. 2) to facilitate electrically connecting the electrically conductive pathways 30 with the ECG monitoring device 1002. The base portion 22 of the set 10 may directly connect to the ECG monitoring device 1002, or may connect to the device 1002 using any suitable extension 1006 as is shown in the exemplary embodiment. The ECG monitoring device 1002 may be any suitable processing device that is capable of performing signal processing and computational operations to convert the raw electrical signals from the electrodes 28 into meaningful ECG information that can be displayed on a monitor 1004 and/or printed out for review by a physician.

In operation, and referring to FIGS. 1 and 10, the base portion 22 of the ribbonized cable core 12 is placed on or adjacent a patient's body. The ribbonized cable core 12 is then separated into the branches 20, such as, but not limited to, one branch 20 at a time. Once separated from the adjacent branches 20, each branch 20 is manipulated to place the corresponding electrode 28 at a desired location on the patient's body. In the exemplary embodiment of FIG. 10, electrode 28a is placed on a chest region of the patient's body adjacent the heart, and the electrodes 28b are placed on the patient's body at the prescribed limb locations RA, LA, RL, and LL of the AHA. However, the ECG system 1000 is not limited to using five electrodes 28, is not limited to the specific locations shown, and each of the electrodes 28 is not limited to being placed at the corresponding location shown. Rather, the ECG system 1000 may use any number of electrodes 18 each located at any suitable location on the patient's body for performing ECG measurements. The particular locations shown in FIG. 10 as well as which electrode 28 of the set 10 is placed at such locations is meant as exemplary only. For example, the set 10 may include more or less branches 20 and electrodes 28 than five, and/or the system 1000 may use more than one electrode lead set (e.g., a set for the chest region and a different set for the limbs). Different locations (e.g., different locations on the chest region and/or the limbs) than those shown may be used in addition or alternative to the locations shown. Moreover, the position of some or all of the electrodes 28 shown in FIG. 10 may be interchanged with one or more other electrodes 28 from the set 10 such that one or more electrodes 28 of the set 10 occupies a different one of the locations shown in FIG. 10 than as is shown in FIG. 10. In the exemplary embodiment, each electrode 28 is intended to be placed at only one specific location on the body (which as indicated in the directly preceding sentence may be a different location than that shown in FIG. 10). However, the locations of some or all of the electrodes 28 of the set 10 may alternatively be interchangeable.

Once all of the electrodes 28 are placed at the desired locations on the patient's body, the ECG monitoring device 1002 receives electrical signals of the electrodes 28 and converts the signals into meaningful ECG information. In some embodiments, the electrode lead set 10 is discarded after a single ECG procedure is performed on the patient or is discarded after a plurality of ECG procedures are preformed on the same patient.

Figure 11:
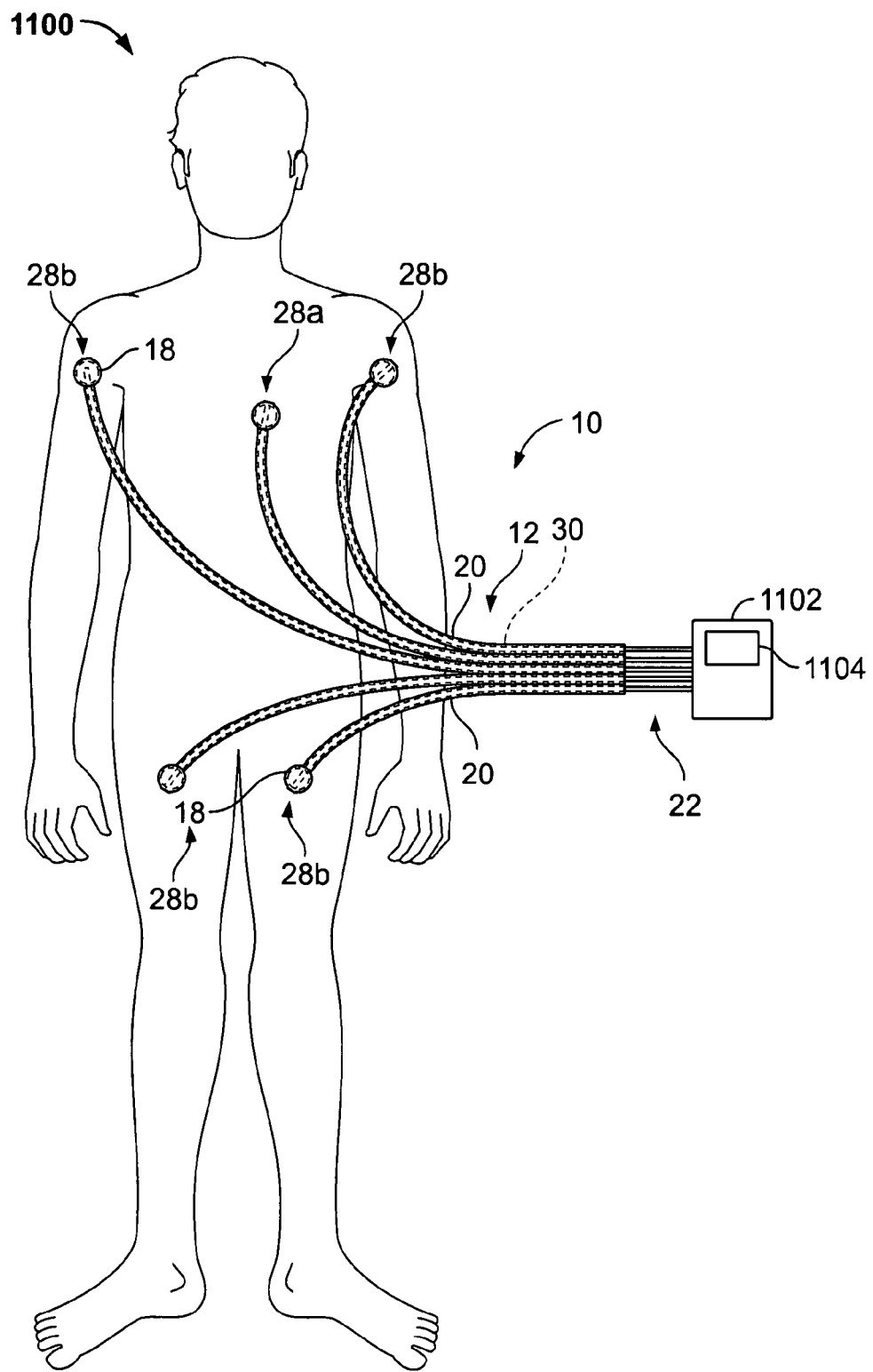

In an alternative embodiment, the electrically conductive pathways 30 are electrically connected to a hand-held patient monitor 1102, as shown in FIG. 11. FIG. 11 is a schematic diagram of an exemplary embodiment of an ECG system 1100 that the electrode lead set embodiments described and illustrated herein may be, but are not limited to being, used with. The hand-held patient monitor 1102 may be any suitable processing device that is capable of performing signal processing and computational operations to convert the raw electrical signals from the electrodes 28 into meaningful ECG information that can be displayed on a monitor 1104 and/or printed out for review by a physician. In another alternative embodiment, the electrically conductive pathways 30 are electrically connected to a wireless transceiver (not shown) such that the ECG signals are transmitted to the hand-held patient monitor 1104 and/or the ECG monitoring device 1002 (FIG. 10) via a wireless connection.

The embodiments thus described provide an electrode lead set having electrically conductive pathways that may be less likely to entangle, that may accommodate differently sized and/or shaped patient bodies, and/or that may facilitate reducing patient-to-patient infection.

Although the electrode lead set embodiments are described and illustrated herein for use with an ECG system, the electrode lead set embodiments described and illustrated herein are not limited to being used with ECG systems for taking ECG measurements. Rather, the electrode lead set embodiments described and illustrated herein may be used with any system for measuring any physiologic information or performing any physiologic procedure, such as, but not limited to, for performing an electroencephalogram (EEG) procedure, for performing muscle and/or nerve stimulation and/or therapy, and/or for performing an electrophysiologic procedure. In some embodiments, the electrode lead sets described and illustrated herein may be a hybrid set that may be used to perform a plurality of different types of physiologic measurements and/or procedures.

Exemplary embodiments are described and/or illustrated herein in detail. The embodiments are not limited to the specific embodiments described herein, but rather, components and/or steps of each embodiment may be utilized independently and separately from other components and/or steps described herein. Each component, and/or each step of one embodiment, can also be used in combination with other components and/or steps of other embodiments. For example, although specific sensor elements are described and/or illustrated with specific attachment devices, each described and/or illustrated sensor element may be used with any of the described and/or illustrated attachment devices as is appropriate. When introducing elements/components/etc. described and/or illustrated herein, the articles "a", "an", "the", "said", and "at least one" are intended to mean that there are one or more of the element(s)/component(s)/etc. The terms "comprising", "including" and "having" are intended to be inclusive and mean that there may be additional element(s)/component(s)/etc. other than the listed element(s)/component(s)/etc. Moreover, the terms "first," "second," and "third," etc. in the claims are used merely as labels, and are not intended to impose numerical requirements on their objects. Further, the limitations of the following claims are not written in means—plus-function format and are not intended to be interpreted based on 35 U.S.C. §112, sixth paragraph, unless and until such claim limitations expressly use the phrase "means for" followed by a statement of function void of further structure.

While the invention has been described in terms of various specific embodiments, those skilled in the art will recognize that the invention can be practiced with modification within the spirit and scope of the claims.

What is claimed is:

1. An electrode lead set for electrical connection to a body, said electrode lead set comprising:
   a flexible ribbonized cable core extending between a proximal end portion and a distal end portion, the distal end portion comprising a plurality of branch end portions that are each configured to hold an electrode, the flexible ribbonized cable core being separable into a plurality of branches that are each joined to adjacent branches by a separable interface prior to separation, each of the plurality of branches comprising a corresponding one of the branch end portions, each branch end portion comprising an electrode housing that is configured to hold the corresponding electrode, and each of the plurality of branches comprising a generally planar ribbon conductor extending along the corresponding branch from the proximal end portion of the ribbonized cable core to the corresponding branch end portion, each generally planar ribbon conductor being at least partially surrounded by an insulating material,
   the electrode housings each comprising a first opening for receiving a distal end portion of the corresponding generally planar ribbon conductor and a second opening for receiving an electrical contact of the corresponding electrode, the first and second openings being relatively arranged such that the distal end portion of the corresponding generally planar ribbon conductor is configured to electrically connect to the electrical contact of the corresponding electrode.

2. The electrode lead set according to claim 1, wherein each of the electrode housings comprises a cover configured to substantially cover the first opening.

3. The electrode lead set according to claim 1, wherein each of the electrode housings comprises a cover configured to substantially cover the corresponding first opening, and each of the covers comprises an extension configured to engage the distal end portion of the corresponding generally planar ribbon conductor to facilitate electrical connection between the corresponding generally planar ribbon conductor and the electrical contact of the corresponding electrode.

4. The electrode lead set according to claim 1, wherein the electrode housings each comprise a first opening for connecting with an electrical contact of the corresponding electrode with a snap-fit connection.

5. The electrode lead set according to claim 1, wherein each of the generally planar ribbon conductors is shielded.

6. The electrode lead set according to claim 1, wherein an electrically conductive material at least partially surrounds the insulating material, and an insulating jacket at least partially surrounds the electrically conductive material.

7. The electrode lead set according to claim 1, wherein prior to separation the plurality of branches are configured such that the branch end portions are maintained in an array at the distal end portion of the substrate core, and each branch end portion within the array is located at about the same distance from the proximal end portion of the ribbonized cable core.

8. The electrode lead set according to claim 1, wherein the electrode lead set is a disposable, single use, electrode lead set.

9. The electrode lead set according to claim 1, wherein the ribbonized cable core is generally planar.

10. The electrode lead set according to claim 1, wherein the ribbonized cable core comprises a base portion that includes the proximal end portion, and, after separation of the branches, each branch is only connected to adjacent branches at the base portion.

11. The electrode lead set according to claim 1, wherein after separation of the branches, each branch end portion is selectively positionable at a plurality of different positions relative to the branch end portion of each of the other branches such that each branch end portion can be positioned at about the same location on at least one of differently sized and differently shaped bodies.

12. An electrode lead set assembly for electrical connection to a body, said electrode lead set assembly comprising:
  a flexible ribbonized cable core extending between a proximal end portion and a distal end portion, the distal end portion comprising a plurality of branch end portions, the flexible ribbonized cable core being separable into a plurality of branches that are each joined to adjacent branches by a separable interface prior to separation, each of the plurality of branches comprising a corresponding one of the branch end portions, wherein each of the plurality of branches comprises a generally planar ribbon conductor extending along the corresponding branch from the proximal end portion of the ribbonized cable core to the corresponding branch end portion, each generally planar ribbon conductor being at least partially surrounded by an insulating material; and
  a plurality of electrodes each being held by a corresponding branch end portion of a different branch of the plurality of branches,
  the branch end portions each comprising an electrode housing that holds the corresponding electrode, the electrode housings each comprising a first opening having a distal end portion of the corresponding generally planar ribbon conductor at least partially received therein and a second opening having an electrical contact of the corresponding electrode at least partially received therein, the first and second openings being relatively arranged such that the distal end portion of the corresponding generally planar ribbon conductor is electrically connected to the electrical contact of the corresponding electrode, and
  each of the electrode housings comprising a cover configured to substantially cover the corresponding first opening, and each of the covers comprising an extension configured to engage the distal end portion of the corresponding generally planar ribbon conductor when the cover substantially covers the corresponding first opening to facilitate electrical connection between the corresponding generally planar ribbon conductor and the electrical contact of the corresponding electrode.

13. The electrode lead set assembly according to claim 12, wherein each electrode comprises an electrically conductive gel that is applied to the electrode housing in direct engagement with the a distal end portion of the corresponding generally planar ribbon conductor.

14. The electrode lead set assembly according to claim 12, wherein an electrically conductive material at least partially surrounds the insulating material, and an insulating jacket at least partially surrounds the electrically conductive material.

15. The electrode lead set assembly according to claim 12, wherein the electrode lead set is a disposable, single use, electrode lead set.

16. An electrode lead set for electrical connection to a body, said electrode lead set comprising:
  a flexible ribbonized cable core extending between a proximal end portion and a distal end portion, the distal end portion comprising a plurality of branch end portions that are each configured to hold an electrode, the flexible ribbonized cable core being separable into a plurality of branches that are each joined to adjacent branches by a separable interface prior to separation, each of the plurality of branches comprising a corresponding one of the branch end portions, wherein prior to separation the plurality of branches are configured such that the branch end portions are maintained in an array at the distal end portion of the substrate core, and each branch end portion within the array is located at about the same distance from the proximal end portion of the ribbonized cable core,
  the branch end portions each comprising an electrode housing that holds the corresponding electrode, the electrode housings each comprising a first opening having a distal end portion of the corresponding generally planar ribbon conductor at least partially received therein and a second opening having an electrical contact of the corresponding electrode at least partially received therein, the first and second openings being relatively arranged such that the distal end portion of the corresponding generally planar ribbon conductor is electrically connected to the electrical contact of the corresponding electrode, and
  each of the electrode housings comprising a cover configured to substantially cover the corresponding first opening, and each of the covers comprising an extension configured to engage the distal end portion of the corresponding generally planar ribbon conductor when the cover substantially covers the corresponding first opening to facilitate electrical connection between the corresponding generally planar ribbon conductor and the electrical contact of the corresponding electrode.

* * * * *